US009060508B2

(12) United States Patent
Anti et al.

(10) Patent No.: US 9,060,508 B2
(45) Date of Patent: Jun. 23, 2015

(54) HIGH-PERFORMANCE EXTENDED TARGET TEMPERATURE CONTAINERS

(76) Inventors: Alex N. Anti, Centreville, VA (US); Victor N. Anti, Centreville, VA (US)

( * ) Notice: Subject to any disclaimer, the term of this patent is extended or adjusted under 35 U.S.C. 154(b) by 420 days.

(21) Appl. No.: 13/552,142

(22) Filed: Jul. 18, 2012

(65) Prior Publication Data

US 2014/0021208 A1 Jan. 23, 2014

(51) Int. Cl.
*F25D 3/08* (2006.01)
*A01N 1/02* (2006.01)

(52) U.S. Cl.
CPC .............. *A01N 1/0273* (2013.01); *F25D 3/08* (2013.01)

(58) Field of Classification Search
CPC ... F25D 3/00; F25D 2400/12; F25D 2303/00; F25D 2303/082
USPC ............... 62/457.2, 457.1; 220/592.01, 592.2
See application file for complete search history.

(56) References Cited

U.S. PATENT DOCUMENTS

| | | | | |
|---|---|---|---|---|
| 3,905,540 | A * | 9/1975 | Abert | 229/125.19 |
| 4,311,022 | A * | 1/1982 | Hall | 62/457.2 |
| 4,444,354 | A * | 4/1984 | Staelgraeve | 229/125.19 |
| 5,493,874 | A * | 2/1996 | Landgrebe | 62/457.2 |
| 6,230,515 | B1 * | 5/2001 | Wiesman | 62/457.1 |
| 6,381,981 | B1 * | 5/2002 | Yaddgo et al. | 62/372 |
| 6,405,556 | B1 * | 6/2002 | Bucholz | 62/457.2 |
| 7,240,513 | B1 * | 7/2007 | Conforti | 62/457.2 |
| 8,074,465 | B2 * | 12/2011 | Heroux et al. | 62/371 |
| 2002/0050147 | A1 * | 5/2002 | Mai et al. | 62/457.2 |
| 2005/0178142 | A1 * | 8/2005 | Perry et al. | 62/371 |
| 2007/0028642 | A1 * | 2/2007 | Glade et al. | 62/371 |
| 2008/0276643 | A1 | 11/2008 | Heroux et al. | |
| 2009/0078699 | A1 * | 3/2009 | Mustafa et al. | 220/1.5 |
| 2011/0147391 | A1 * | 6/2011 | Corder et al. | 220/592.27 |

OTHER PUBLICATIONS

Kreith, Frank et al., The CRC Handbook of Mechanical Engineering, 2004, CRC Press, Second Edition, Chapter 12, p. 26.*

* cited by examiner

*Primary Examiner* — Cheryl J Tyler
*Assistant Examiner* — David Teitelbaum
(74) *Attorney, Agent, or Firm* — Henry J. Recla

(57) ABSTRACT

Reusable and recyclable target temperature storage and shipping containers designed to maintain the content therein within desired temperature levels for greatly extended periods of time are disclosed. A First species is customized to maintain refrigeration temperatures for extended periods of time and the Second species maintains freezing temperatures for extended periods of time. Both species models include containers having outer protective layers and inner insulating layers as well as a cavity for holding payload being stored or shipped, and one or more areas for holding passive coolants in a predetermined relationship to the products within specific target temperatures. The different species provide cold or freezing temperatures in reusable or disposable models for various applications. The main containers are substantially airtight when sealed for storage or shipping and includes an outer box, inner insulation, internal dividers, and different temperature controlling coolants designed for various temperature maintenance requirements of temperature-sensitive content.

33 Claims, 16 Drawing Sheets

HIGH-PERFORMANCE EXTENDED TARGET TEMPERATURE CONTAINERS

FIELD OF THE INVENTIONS

The disclosed inventions are designed to cater mainly to the needs of medical and environmental testing laboratories and, in general, the medical care markets for the dispatch and storage of specimens, chemicals, fluids, solid samples, tissue, and organs within desirable temperature ranges for extended periods of time considerably beyond currently available passive coolant storage and shipping containers solutions. All materials used in the construction of the containers are non-toxic, disposable, reusable and recyclable. The disclosed inventions are designed mainly for storing or transporting items within a consistent temperature range for an extended period of time. Their economical, ease-of-use, durable, light weight, and recyclable materials make them unique in many market segments as high-performance "coolers" for extended storage and long-range shipping or multi-city transportation.

BACKGROUND

Main Market Spaces: Extended target temperature shipping containers systems of the type cater mainly to businesses and institutions that store, ship or transport temperature and time-sensitive products locally and from coast to coast and worldwide. One example of such systems is disclosed in U.S. Patent Application Publication No. 2008/0276643.

The clinical testing market is a primary user of such systems which currently use EPS (Expanded Polystyrene) foam insulated shipping coolers. Hospitals are responsible for generating 49% of all clinical test orders but perform only 63% of all tests within their own laboratories. There are an estimated 6,500 hospital labs in the US alone ranging from small and simple to large and complex.

Other users of these containers include hospital laboratories' specimen staging, hospital pharmacies, blood supply, plasma and serum, forensic medical, and organ and tissue storage. These applications extend to military field clinics and hospitals as well as disaster relief support operations.

Test Send Out (TSO): Although usually esoteric, what hospitals actually send out to reference labs is minor in comparison to the overall testing market. Even though it is a relatively minor opportunity, capturing hospital TSO is the one opportunity for virtually every commercial laboratory. The short temperature control time that typical coolers provide has greatly limited the opportunities for many labs to enhance their local logistics and/or expand beyond their markets.

Hospital Test Mix is More Esoteric: Most hospitals perform the more frequently ordered, highly automated, or fairly simple tests in-house. What a hospital typically sends to a commercial lab is usually the more esoteric or complex tests. As a result, hospital TSO often are more expensive, complex tests that need to travel within the right target temperature range.

Clinical Reference Labs: A number of boutique and regional labs have to send the more complex testing to large labs. Their need for controlled target temperature shipping containers is critical especially when time and distance limit their current reach. Comparative testing shows that the performance of the containers of the present inventions triples those of standard EPS coolers with the limited cooling agents dictated by the airline industry. The same hugely improved performance over the same standard coolers when compared to the present inventions triples as well when coolant volumes are unlimited for freezing conditions.

Other: The global presence of many reference laboratories adds to the need for sturdy, economical, green "shippers" that provide longer target temperatures. For example, lab operations in India will require a 48 hours target temperature capability to capitalize on such new markets opportunities. The present invention containers prove to be the perfect carrier for such applications where payload needs to cross continents at safe temperatures.

Medical supplies storage including hospital floor pharmaceuticals, blood, plasma, saline solutions, and others are often a great concern. Large electrical temperature-controlled equipments cannot offer the flexibility of easy-to-carry compact coolers.

Blood banks also have a consistent logistical problem when considerable volumes of blood supply is lost every year because of loss of safe temperature control despite their huge investments in equipment and transit systems. The batching capability of the present invention containers along with their high performance prove to be a unique added storage and transportation capability to all blood and blood related products.

Current Conditions: Current EPS insulated containers typically maintain 32° F. (0° C.) for 24 hours after 5 lbs dry ice evaporate in 18-20 hours. A significant number of specimens are rejected for testing due to specimen thaw. Critical frozen specimens are needed for many coagulation and nucleic acid tests. The same market standard EPS containers perform more poorly when refrigeration temperatures (35-45° F. or 2-8° C.) are needed. This moderately cold temperature environment is often more difficult to achieve even for shorter periods. The disclosed containers of the present invention provide both solutions at triple the time-performance in sturdier, lightweight, recyclable, and green alternatives while maintaining the preferred target temperature range for each application.

Shipping products within target temperatures for extended periods of time is still a challenge. Storage and shipping solutions for products below ambient temperature are a consistently growing market segment of the shipping supplies industry. This growth is driven partly by the need of medical institutions to transport specimens within certain temperature limits to other locations extending their collaborative testing reach. Other medical and pharmaceutical market segments face similar challenges where their preferred target temperature performance needs require prohibitive investments in additional equipment and logistics systems that often render negative return on investment (ROI).

The controlled temperature packaging (CTP) market includes multiple size temperature level segments ranging from larger than pallet (usually cooled by mechanical refrigeration providing days or weeks of temperature control), one cubic foot to a pallet (typically using dry ice or gel refrigerants inside EPS insulated containers limiting cold to freezing temps to 18-24 hours), and less than one cubic foot (a popular however challenging size limited by volume and performance features).

The present inventions respond to the need for smaller containers, providing greatly extended controlled target temperatures time, economically constructed, recyclable, and using self-sufficient passive refrigeration.

SUMMARY OF THE INVENTIONS

The disclosed HIGH-PERFORMANCE INSULATED STORAGE AND SHIPPING CONTAINERS are capable of withstanding the rigors associated with storage and shipping parcels in commerce. The disclosed containers of the present inventions focus on solutions for the storage and shipping supplies segment usually referred to as controlled temperature packaging (CTP) and extended target temperature, which in this case means "longer" performance within maximum acceptable temperature levels. Their structure is designed to withstand rough handling particularly when their payload is fragile and requires extended controlled temperature. Advantageously, the containers may be packed with a variety of materials and shapes of contents. Custom inner containers and cushioning materials can be added to organize particular contents and permits the overall size of the main container to be standardized.

In accordance with the present inventions, the disclosed containers provide temperature sensitive storage and transport containers for packaging medical, biological and pharmaceutical products. In particular, the present inventions provide thermally insulated container systems for storage and transportation which are capable of maintaining payload at a desirable temperature range for a long period of time when equipped with coolants to ensure adequate levels through extended storage time or through transit time and upon delivery.

The present inventions provide thermally insulated container systems that include closable containers having a thermally insulated portion, the containers being configured for storage and shipment of medical and pharmaceutical products. The systems may also include canisters or partitions inside the containers. The canisters as well as the partitions may be configured for holding or separating the products, and/or various refrigerants and other insulators within the containers. The refrigerants and the insulators are configured to hold internal temperatures in the ranges of <32° F. (<0° C.) or 35° to 45° F. (2 to 8° C.) for a period of at least 72 hours when the containers have been sealed closed and maintained in room temperature and using only USDOT- and IATA-approved volume of dry-ice and coolants for air transport for freezing or refrigeration.

The main aspect of the present inventions includes a thermal insulating enclosure system formed from at least five separate nesting, thermally insulating materials including corrugated carton panels and high-density EPS that define the interior volume as well as a multi-layers insulated payload area bottom.

The thermal insulating enclosure system is comprised of an outer corrugated carton box, a corrugated carton box liner, a large insulating EPS box positioned within the outer box/liner assembly, and a smaller EPS inner box, wherein the insulating box surrounds the inner box. In accordance with another aspect, a tight fit is produced between the insulating box and the inner box, the insulating box and the outer box, and wherein the boxes are not removable from one another. In accordance with another aspect, at least one layer of tape must be wrapped around the insulating box to seal it for storage or shipping.

From the following detailed description of various preferred embodiments, it will be apparent that the present inventions provide significant advance in the technology of thermal storage and transportation containers. Particularly significant in this regard is the potential the invention affords for providing a high quality, low cost thermal storage container capable of keeping items chilled or frozen for extended periods of time exceeding any other such products' performance. Additional features and advantages of various preferred embodiments will be better understood in view of the detailed description provided below.

First Species: Target Refrigeration Temperature Range 35° to 45° F. (2 to 8° C.)

The embodiment of the First Species illustrated in FIGS. 8-12 is a container comprising of a rigid insulated box including a base portion and sides that extend from the base portion, wherein inside surfaces of the sides and the base portion together define a first enclosed space with the opening at an end of the sides that is opposite from the base, and a lid matching the base design to seal the box opening. A corrugated cardboard liner is also included inside the box thereby reinforcing the sides which are glued together to form the shell. This first contents container defines the main enclosed space comprising a separate lid which completes the first inside portion of the overall system.

A second contents container including a second tight-closing lid is nested inside the first contents container thereby substantially preventing the controlled temperature air from communication with the outside. A payload area divider hereby named COOL SHIELD separates the contents into two parts providing a shielded compartment for the freezing multi-unit gel component hereby named COOL BATTERY to chill the stored/transported products while preventing the payload from freezing.

Second Species: Target Freezing Temperature Range<32° F. (<0° C.)

The embodiment of the Second Species illustrated in FIGS. 13-16 is a similar container to the one used for the First Species comprising of a rigid insulated box including a base portion and sides that extend from the base portion, wherein inside surfaces of the sides and the base portion together define a first enclosed space with the opening at an end of the sides that is opposite from the base, and a lid matching the base design to seal the box opening. A liner is also included inside the box thereby reinforcing the sides which are glued together to form the shell. This first contents container defines the main enclosed space comprising a separate lid which completes the first inside portion of the overall system.

A second contents container including a second tight-closing lid is nested inside the first contents container thereby substantially preventing the controlled temperature air from communication with the outside. An inner-base component hereby named FREEZING RELAY comprising multiple freezing gel containers creates the back-up coolant that extends the freezing temperature performance of the dry-ice main passive coolant/freezer. The payload is placed on the frozen FREEZING RELAY base to allow the dry-ice coolant to cover above and around it and filling most of the interior portion and receive adequate amounts of dry ice (USDOT- and IATA-approved volume for air transport only). Additional dry-ice use extends the container's temperature control performance considerably.

BRIEF DESCRIPTION OF THE DRAWINGS

FIG. 1 is a section view of the Common Embodiment of the HIGH-PERFORMANCE INSULATED STORAGE AND SHIPPING CONTAINER showing the closed unit with four boxes (outer corrugated carton box, corrugated carton box liner, large insulating EPS box, small inner EPS box, and their respective lids) nested together.

FIG. 2 is a top view of the inventions' Common Embodiment showing the nested box assembly.

FIG. 3 is a section view of the inventions' Common Embodiment showing the open container (details per FIG. 1).

FIG. 4 is a perspective exploded view of the inventions' Common Embodiment.

FIG. 5 is a perspective view of the outer corrugated carton box unfolded.

FIG. 6 is a perspective view of the corrugated carton box liner unfolded.

FIG. 7 is a perspective view of the outer corrugated box lid unfolded.

Figure 1:
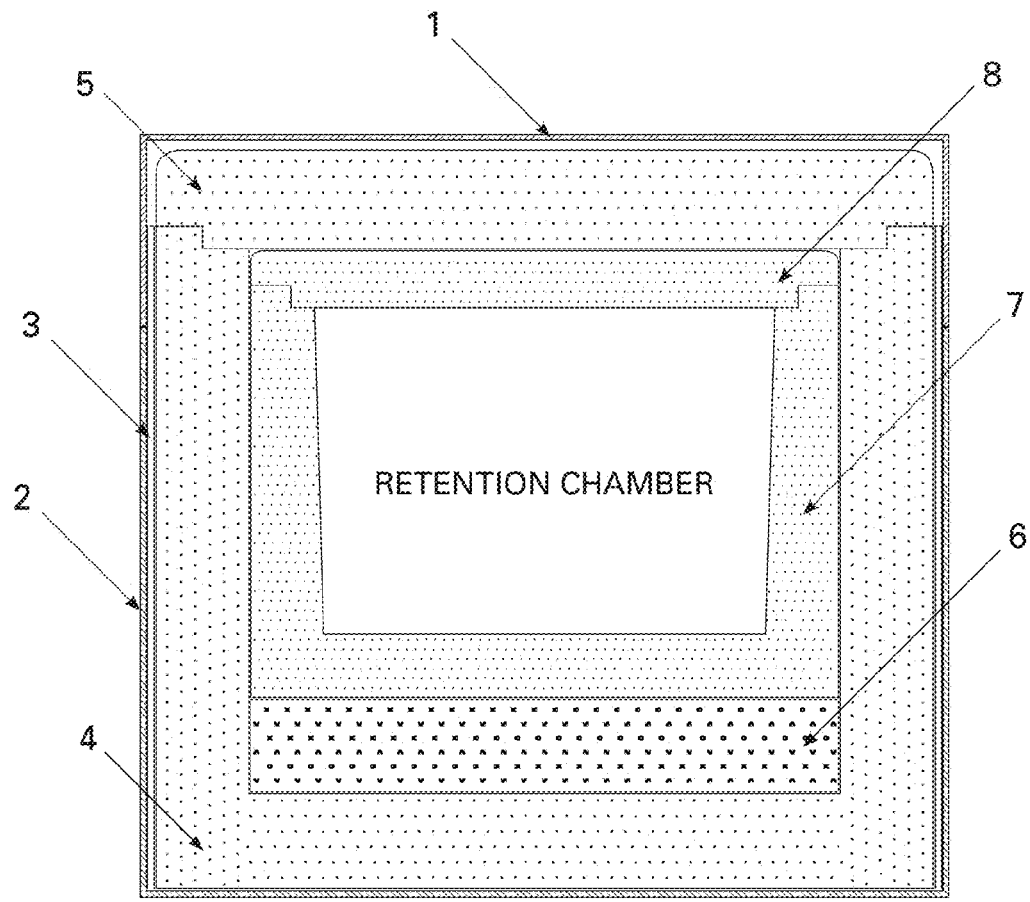
FIGS. 1-7 illustrate structure common to both species, the Common Embodiment.
Figure 2:
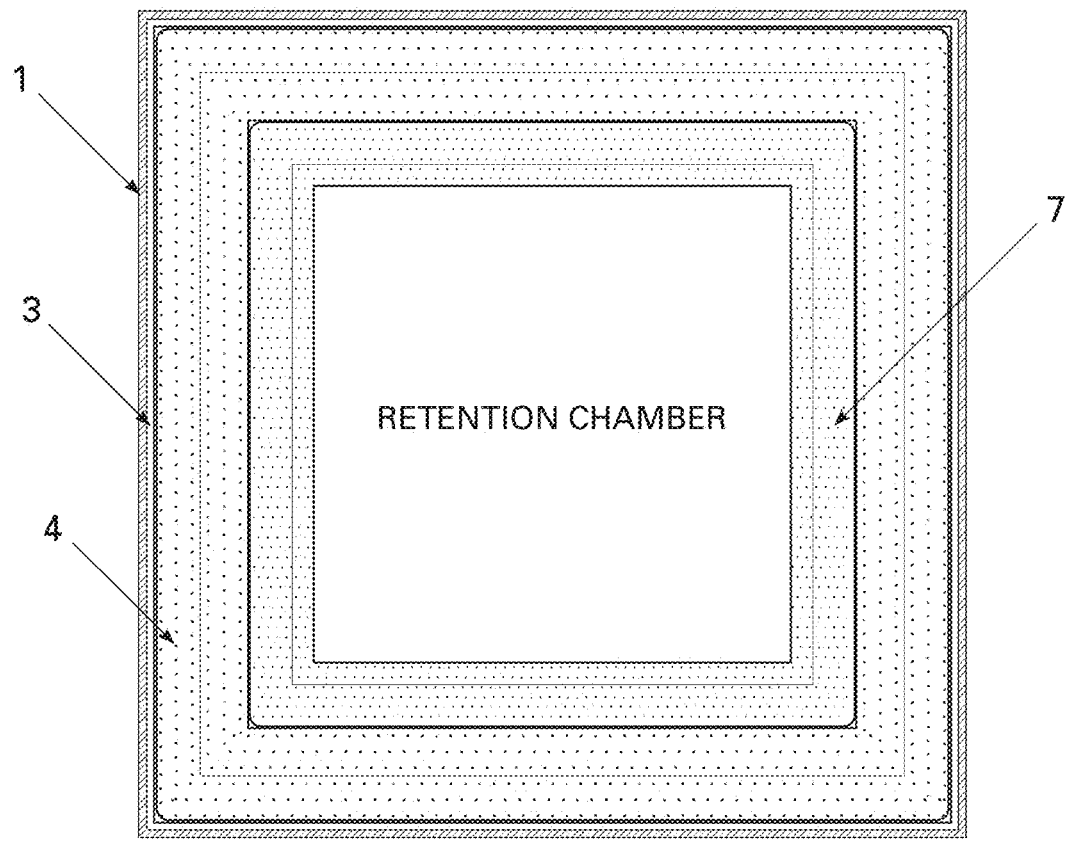
Figure 3:
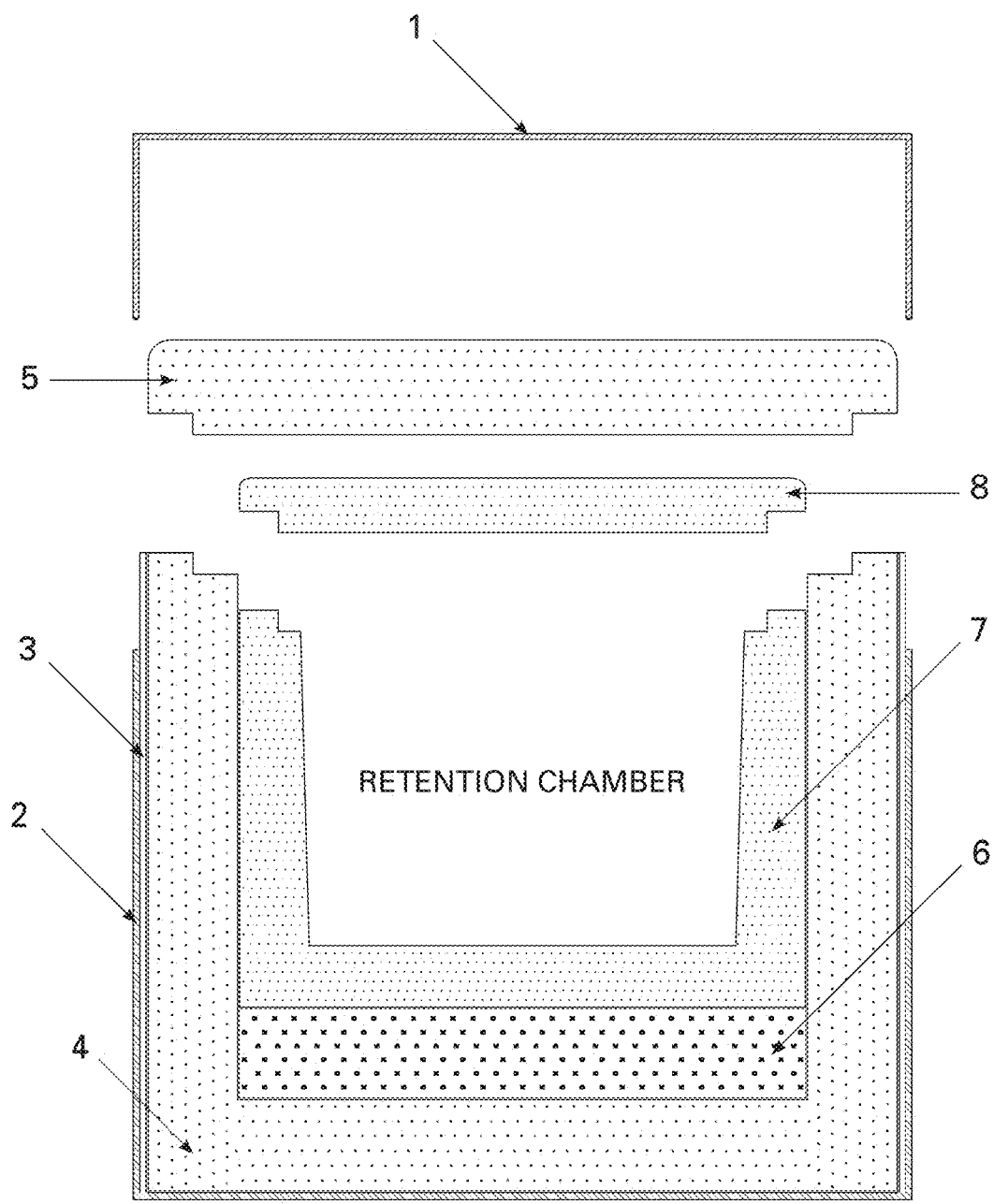
Figure 8:
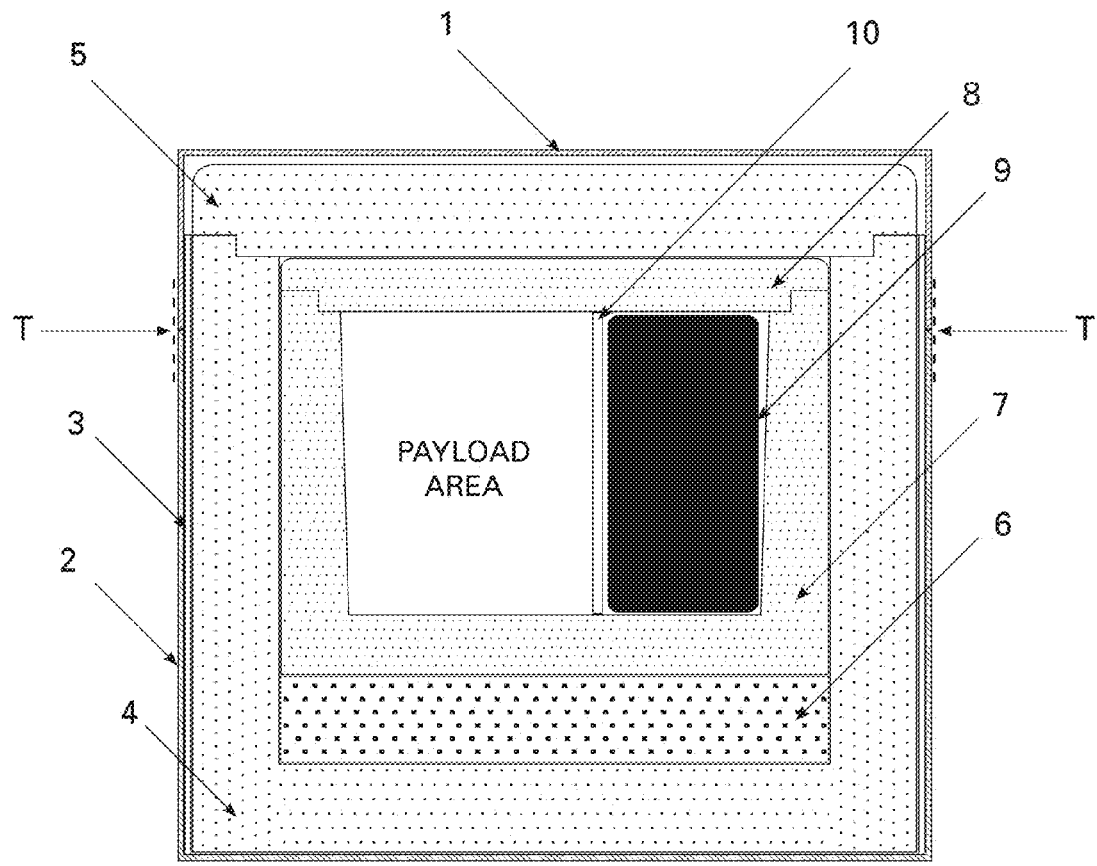

Nomenclature—FIGS. 1 to 7
1. Corrugated cardboard outer-box lid
2. Corrugated cardboard outer-box
3. Corrugated cardboard liner
4. Large EPS insulating box
5. Large EPS insulating box lid
6. EPS interim insulation liner pad
7. Small EPS inner box
8. Small EPS inner box lid First Species:

FIG. 8 is a section view of the Common Embodiment of the HIGH-PERFORMANCE INSULATED STORAGE AND SHIPPING CONTAINER including the First Species setup showing the closed unit with four boxes nested together, the COOL BATTERY unit 9 and the COOL SHIELD 10.

Figure 9:
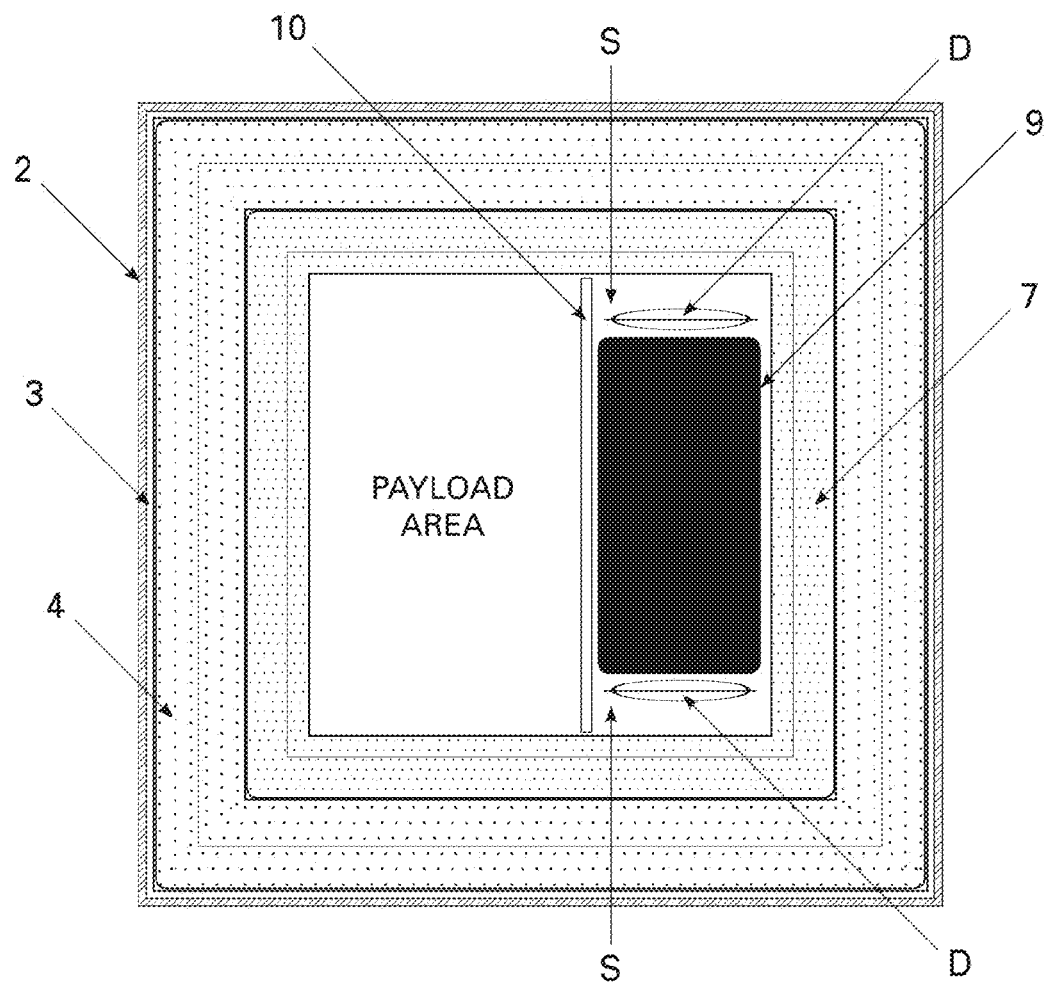

FIG. 9 is a top view of the Common Embodiment with the First Species showing the nested box assembly with the COOL BATTERY unit 9 and the COOL SHIELD 10.

Figure 10:
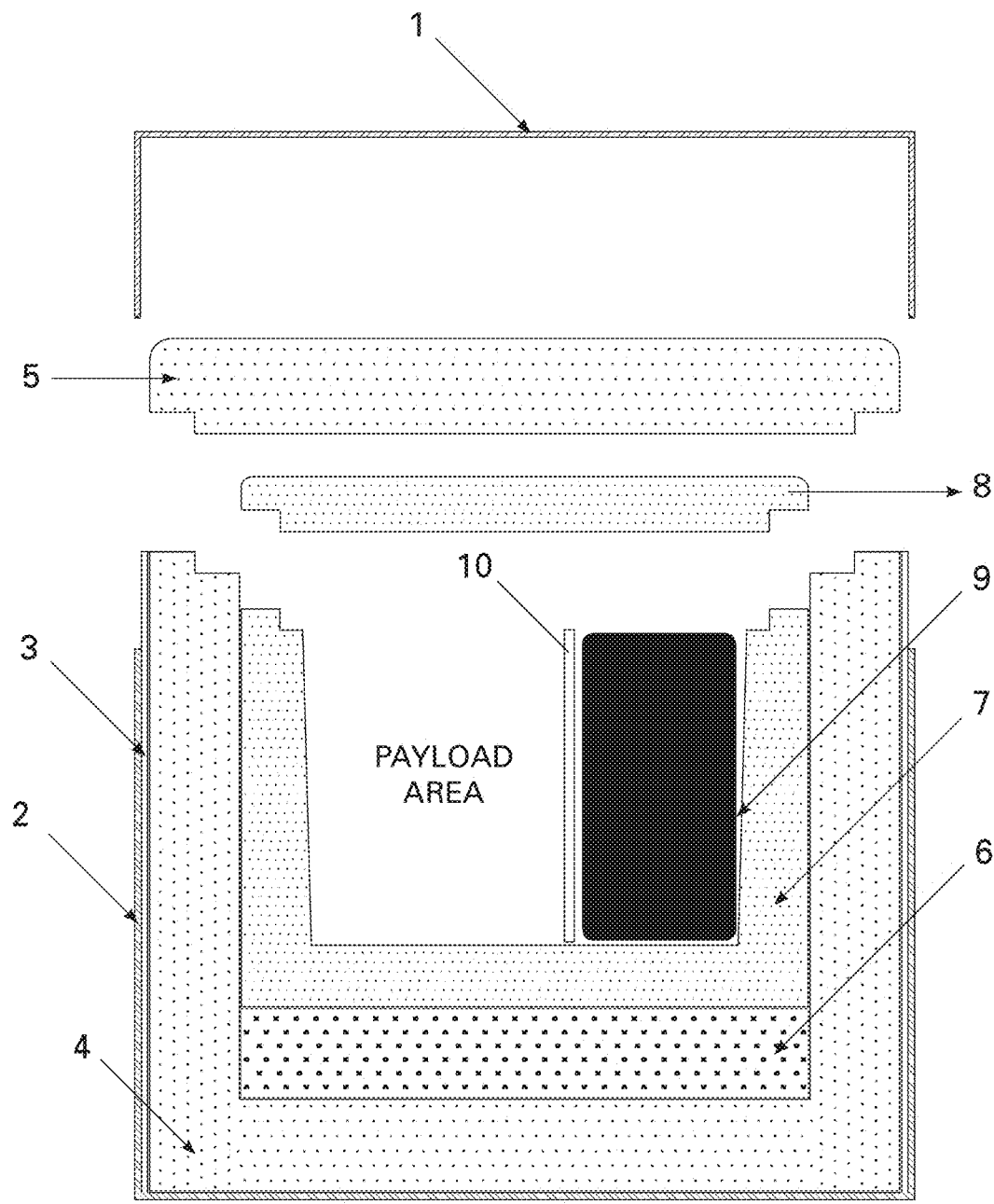

FIG. 10 is a section view of the Common Embodiment with the First Species showing the open container with the COOL BATTERY unit 9 and the COOL SHIELD 10.

Figure 11:
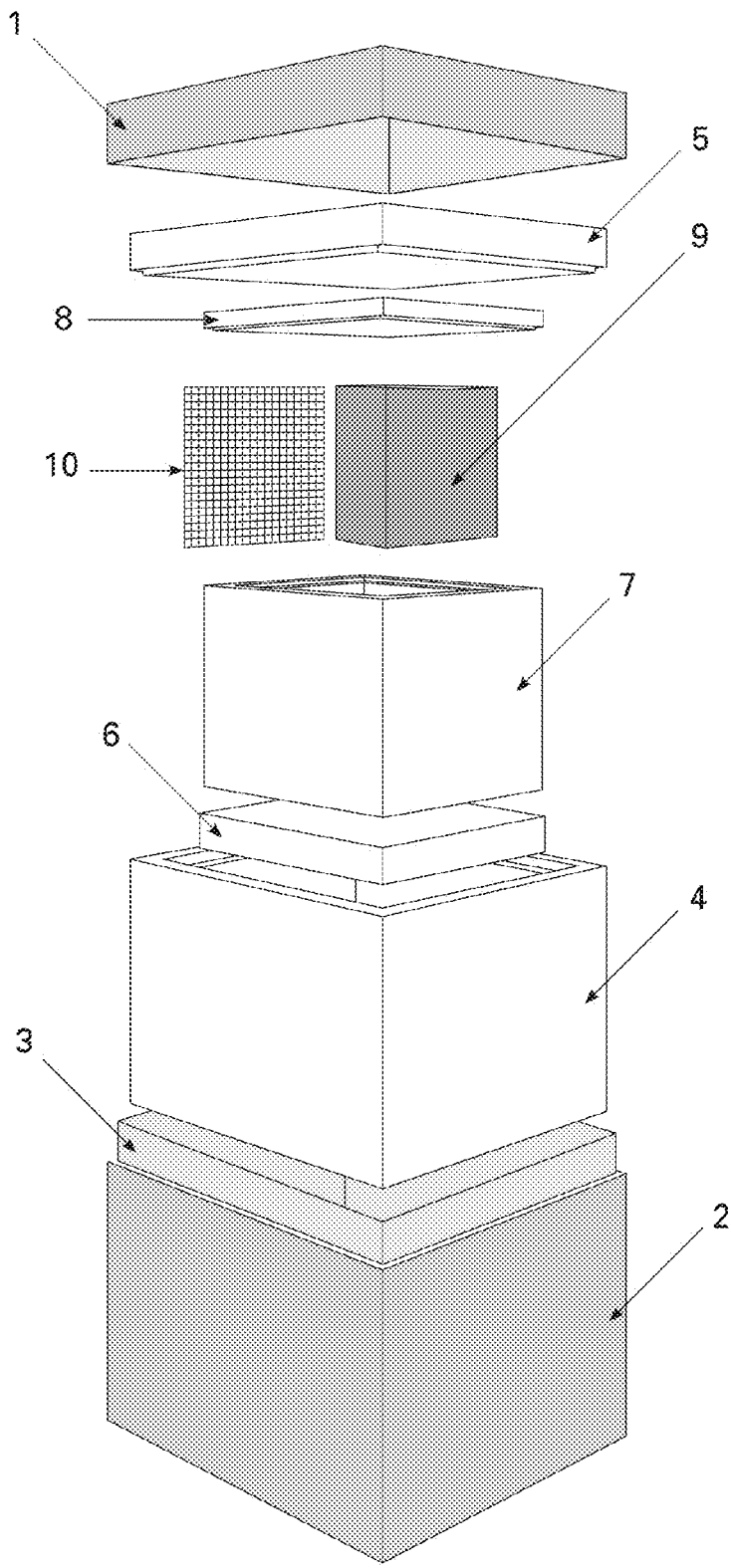
Figures 12A, 12B:
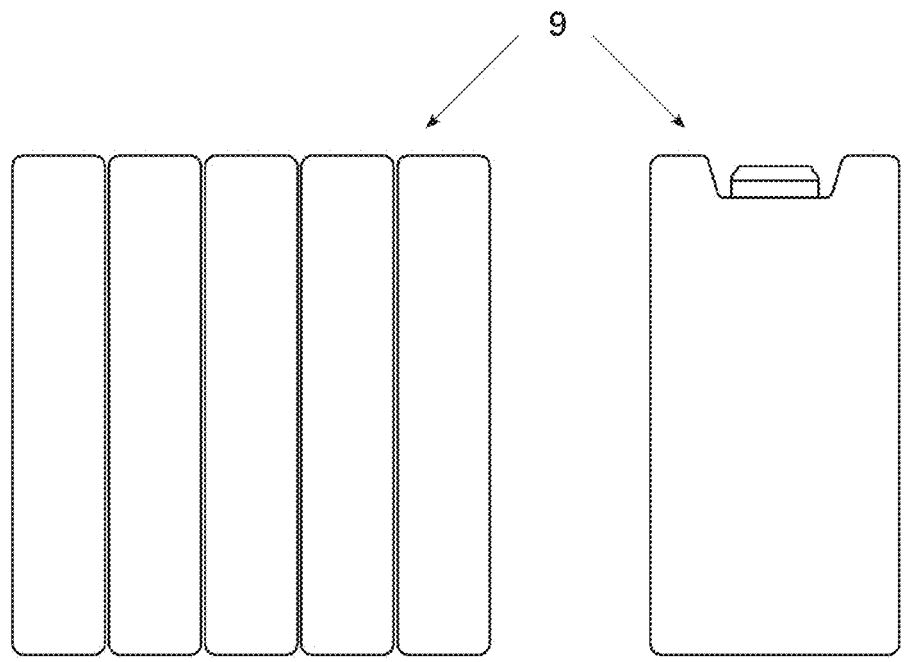
Figures 12C, 12D:
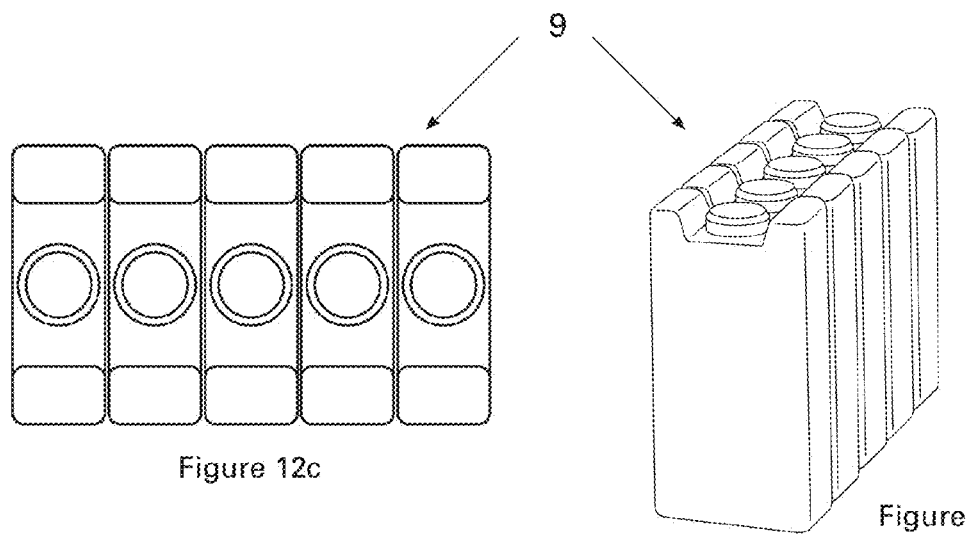

FIG. 11 is a perspective exploded view of the inventions' Common Embodiment with the First Species including the COOL BATTERY unit 9 and the COOL SHIELD 10.

FIGS. 12a-12d are various views of the COOL BATTERY unit 9.

Figure 13:
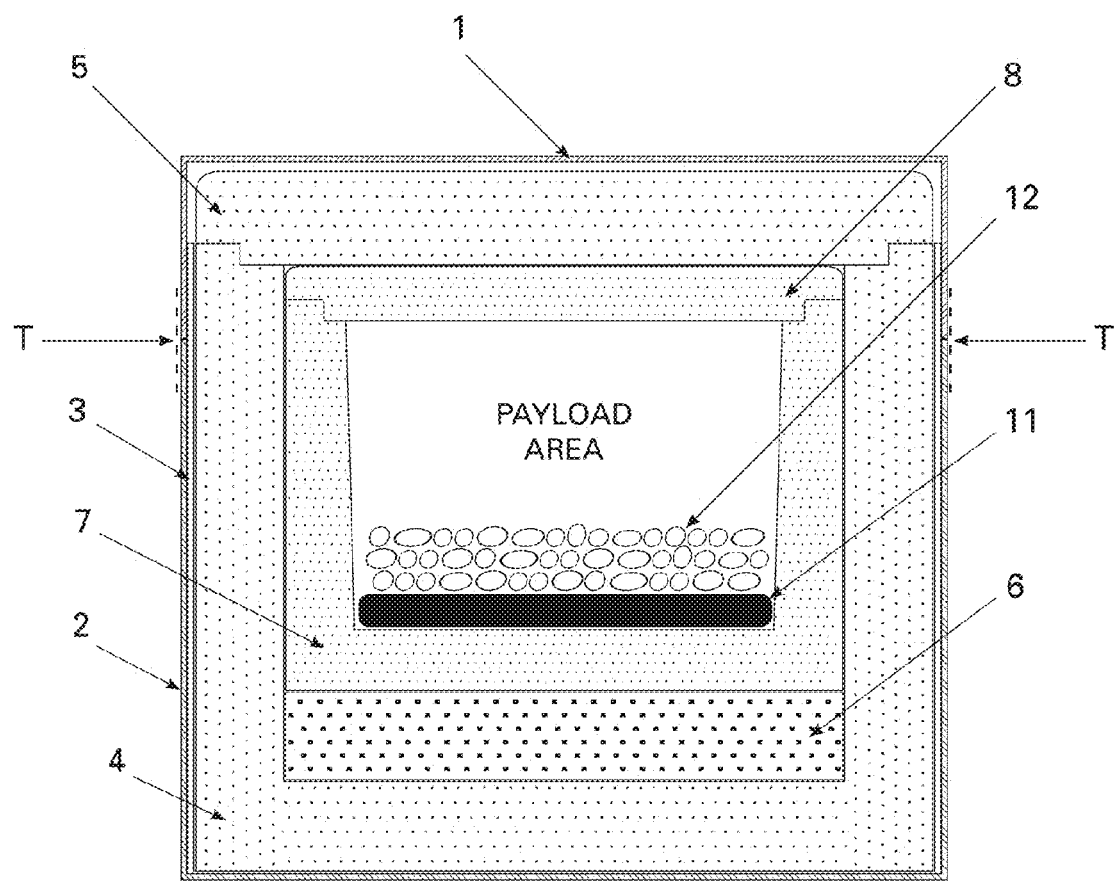

Nomenclature—FIGS. 8 to 12
1. Corrugated cardboard outer-box lid
2. Corrugated cardboard outer-box
3. Corrugated cardboard liner
4. Large EPS insulating box
5. Large EPS insulating box lid
6. EPS interim insulation liner pad
7. Small EPS inner box
8. Small EPS inner box lid
9. COOL BATTERY coolant unit
10. COOLSHIELD protective panel Second Species:

FIG. 13 is a section view of the Common Embodiment of the HIGH-PERFORMANCE INSULATED STORAGE AND SHIPPING CONTAINER including the Second Species setup showing the closed unit with four boxes nested together and the FREEZING RELAY base unit 11.

Figure 14:
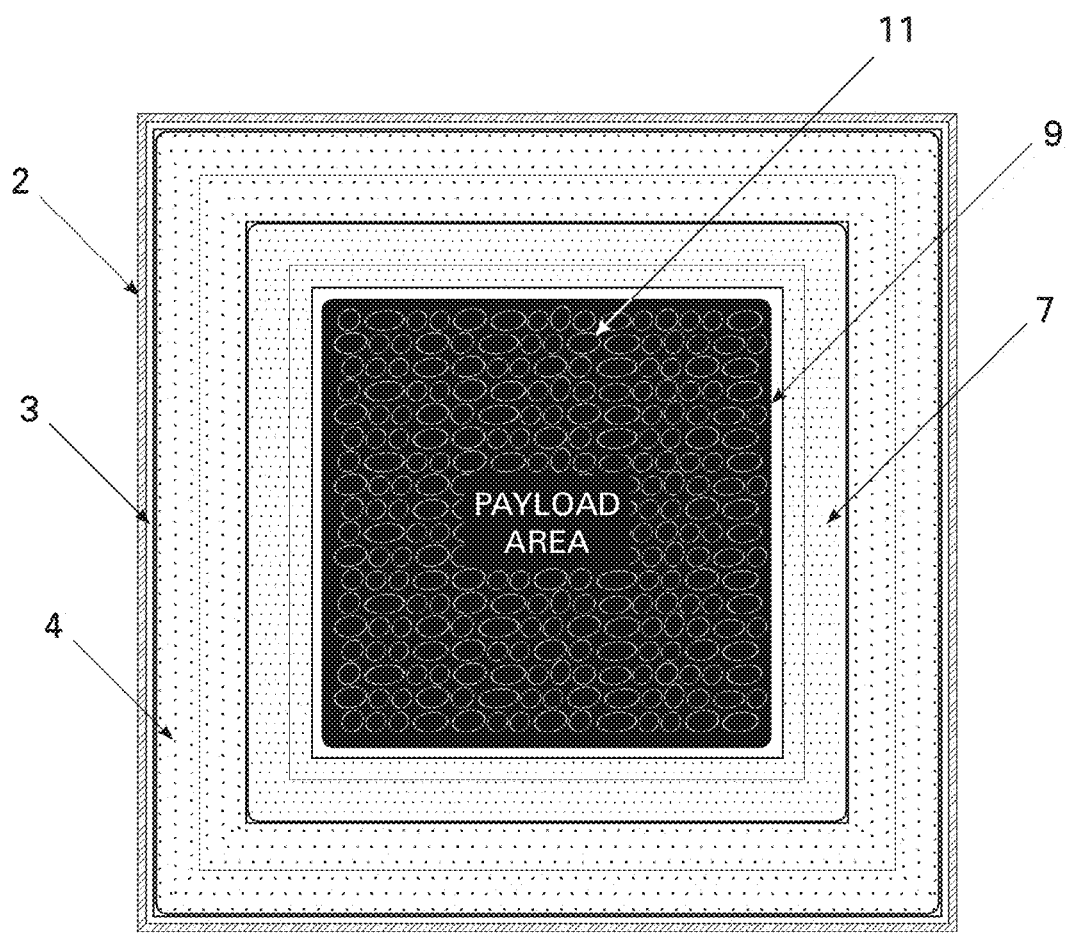

FIG. 14 is a top view of the Common Embodiment with the Second Species showing the nested box assembly with the FREEZING RELAY base unit 11.

Figure 15:
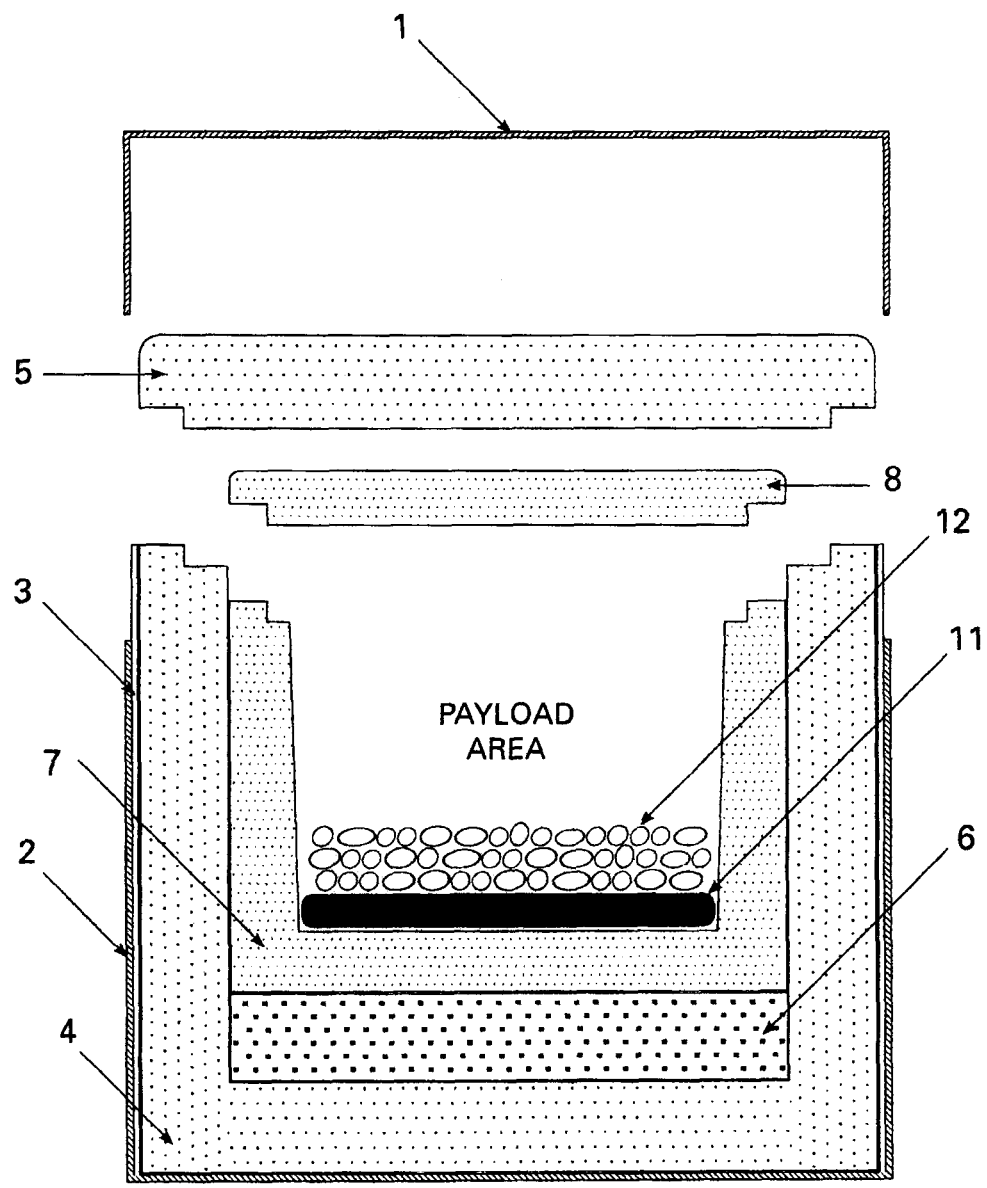

FIG. 15 is a section view of the Common Embodiment with the Second Species showing the open container with the FREEZING RELAY base unit 11.

Figure 16:
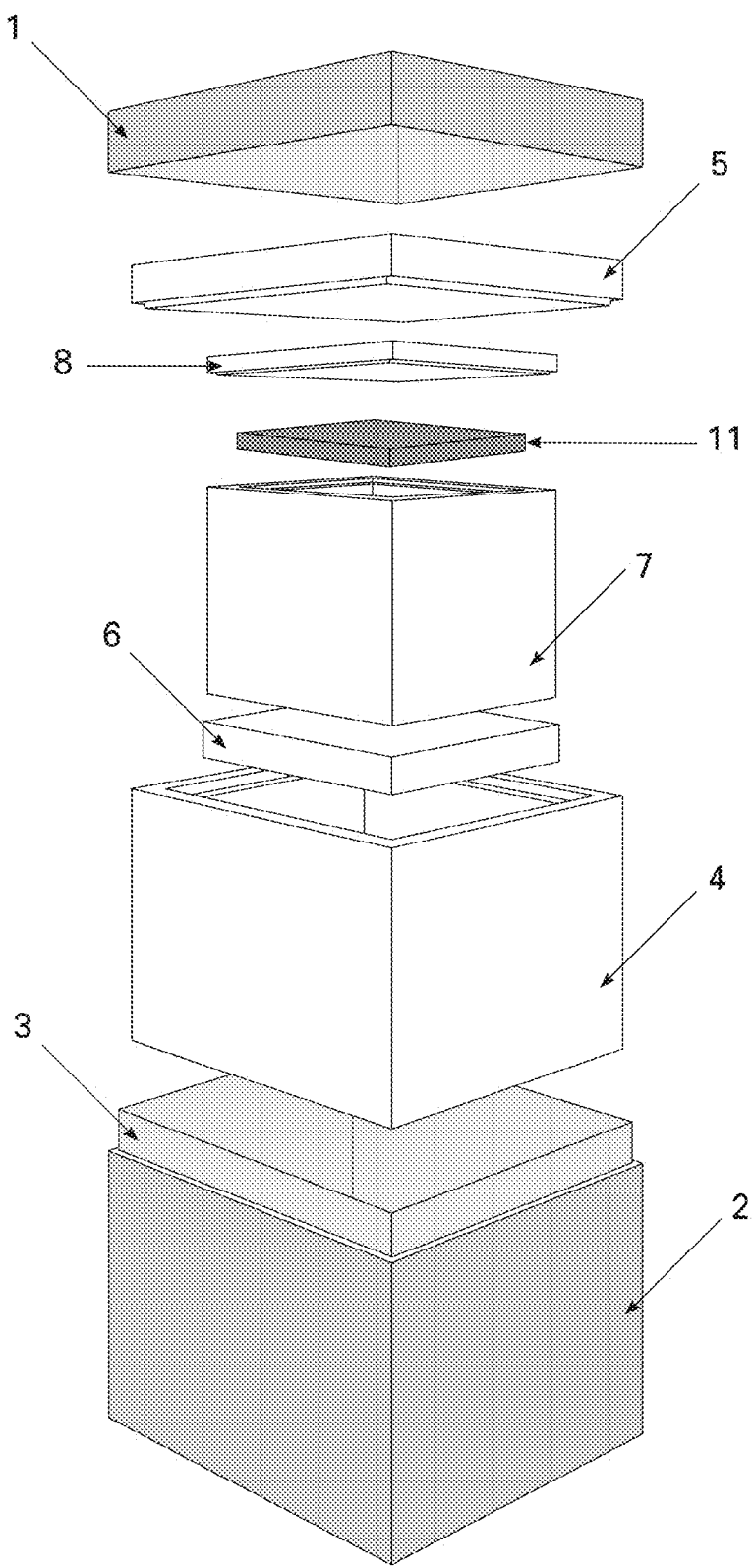

FIG. 16 is a perspective exploded view of the inventions' Common Embodiment with the Second Species including the FREEZING RELAY base unit 11.

Nomenclature—FIGS. 13 to 16
1. Corrugated cardboard outer-box lid
2. Corrugated cardboard outer-box
3. Corrugated cardboard liner
4. Large EPS insulating box
5. Large EPS insulating box lid
6. EPS interim insulation liner pad
7. Small EPS inner box
8. Small EPS inner box lid
11. FREEZING RELAY base unit
12. Dry Ice It should be understood that the appended drawings are not necessarily to scale, showing a somewhat simplified representation of various preferred features illustrative of the basic principles of the inventions. The specific design features of the HIGH-PERFORMANCE INSULATED STORAGE AND SHIPPING CONTAINERS as disclosed herein, including, for example, the specific dimensions of the insulating box, will be determined in part by the particular intended application and use environment. Certain features of the illustrated embodiments have been enlarged or distorted relative to others to enhance visualization and clear understanding. In particular, thin features may be thickened, for example, for clarity of illustration. All references to direction and position, unless otherwise indicated, refer to the orientation illustrated in the drawings.

DETAILED DESCRIPTION OF THE EMBODIMENTS

Our preferred embodiments of the HIGH-PERFORMANCE EXTENDED TARGET TEMPERATURE CONTAINERS disclosed herein and their features illustrate the general principles of the inventions referencing these containers used for the storage or shipping of refrigerated or frozen medical, pharmaceutical and biological products.

High-Performance Insulating Containers—Common Embodiment

Referring to FIGS. 1-7, one of the main aspects of the present inventions is the shared thermal common embodiment or insulating enclosure formed from at least five nesting and thermally insulating materials layers including corrugated carton panels 1, 2 and 3, and high-density EPS layers 4, 5, 7 and 8 that define the interior volume as well as a high-density EPS layer 6 thereby providing a multi-layered insulated payload area bottom. This embodiment is shared by the two different models of our disclosed inventions that provide internal temperature control capabilities for refrigeration or freezing levels.

Both container models include outer protective layers and inner insulating layers as well as a retention chamber for holding the stored or shipped payload, and one or more areas for holding passive coolants in a predetermined relationship to the products and for their specific target temperatures. Ice can be referred to as a phase change material (hereafter "PCM"), which is characterized as a material which changes from a solid to a liquid or gas at a "melting point" temperature, or from a liquid or gas to a solid at the same "melting point" temperature, as thermal energy is either absorbed or released by the PCM, thus acting as a heat source or heat sink, depending on the circumstances.

Figure 5:
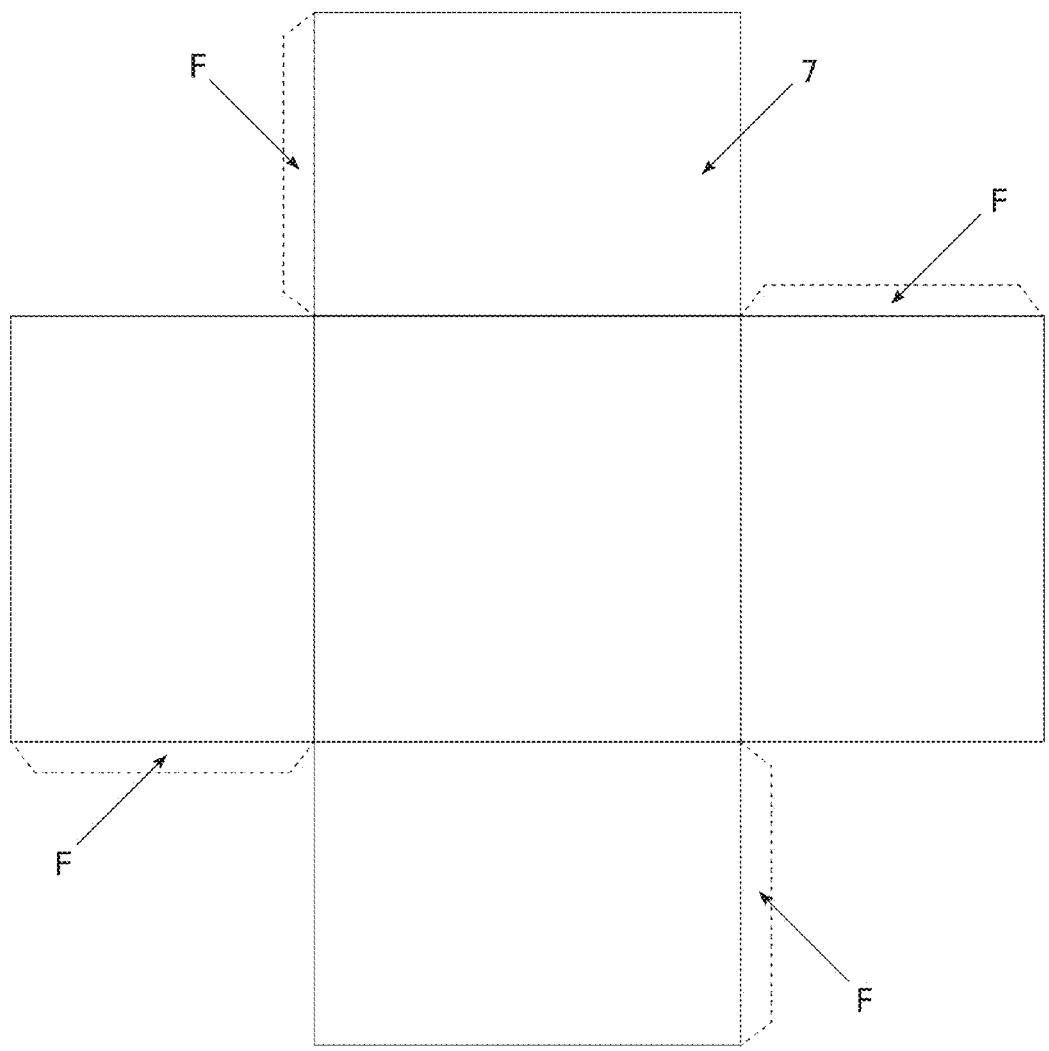
Figure 6:
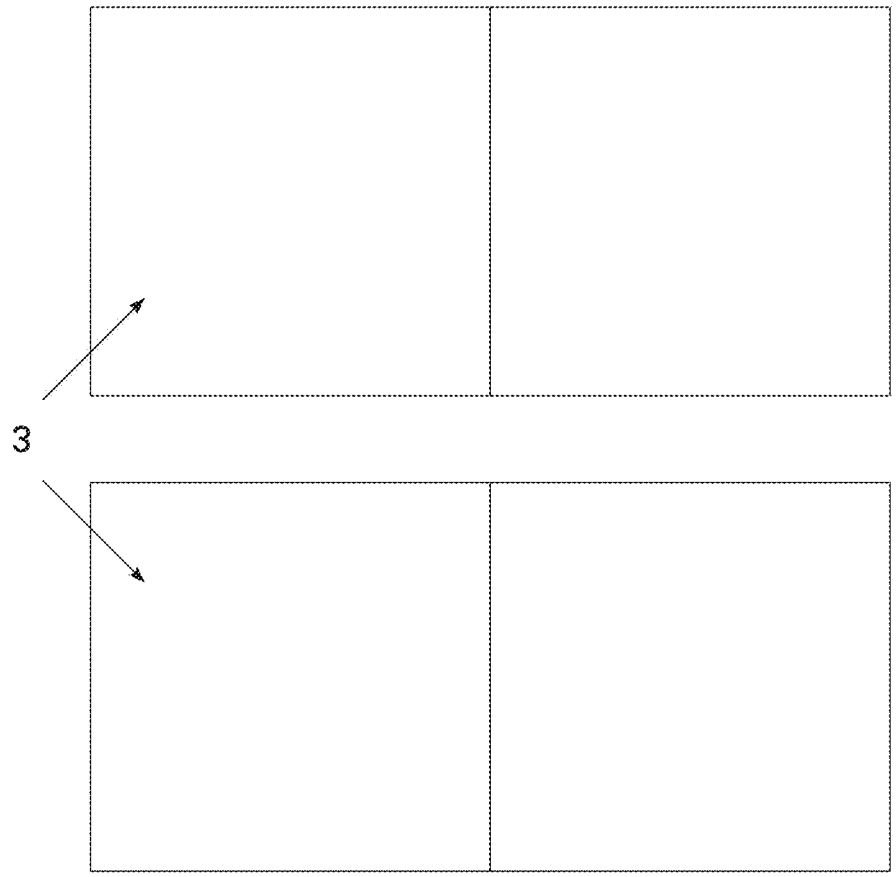
Figure 7:
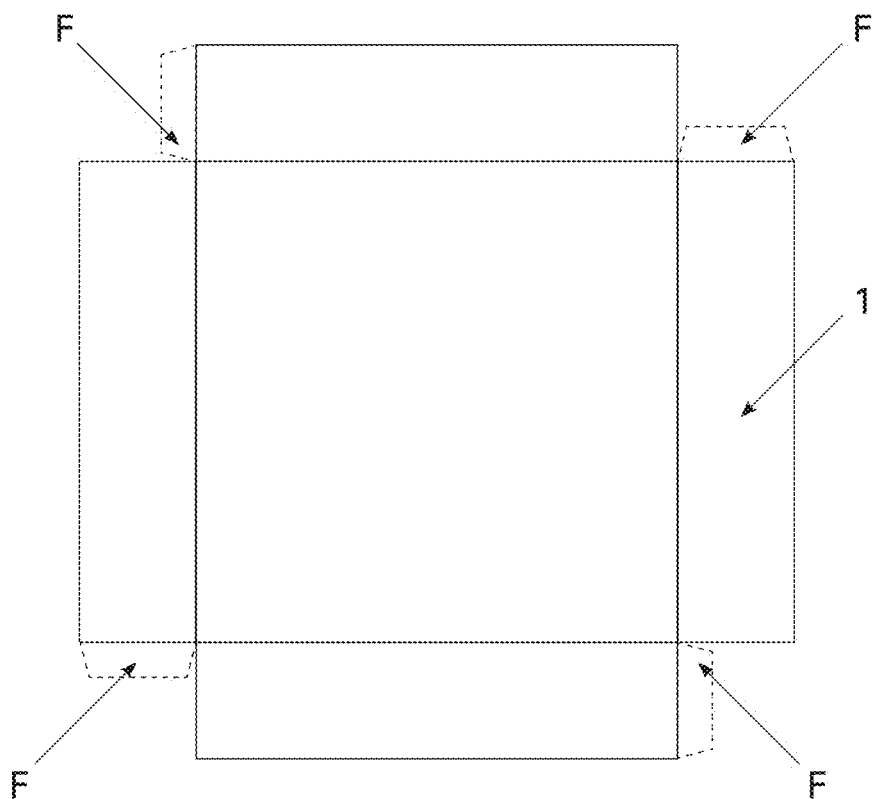

The insulated outer box 2 and cover 1 are each formed of single sheets corrugated cardboard as illustrated in FIGS. 5 and 7. The single sheet outer box includes four side walls extending from a bottom wall and which fold upward to form the box structure. The single sheet outer box lid 1 includes four side walls extending from a top wall which fold downward to form the lid structure. Once folded, the adjacent edges of the outer box and lid may be sealed with conventional packaging tape T although other types of fasteners may be used. For example, each side wall may include a laterally extending flap indicated by dashed lines in FIGS. 5 and 7, which would be adhered to and adjacent side wall. Alternatively, opposite extending side walls could each have two flaps extending laterally therefrom adhered to respective side walls to enclose said side walls. A corrugated carton box liner 3 comprised of two single sheets of corrugated cardboard which are folded in half is illustrated in FIG. 6. The liners are then inserted into the outer box to add a second peripheral insulating layer which also enhances the container's overall rigidity. The liner 3 is adhered to the inner surfaces of the outer box using, for example, cold temperature adhesive. A large inner insulating Expanded Polystyrene (EPS) foam container 4 is then nested inside box liner 3. The inner container 4 is adhered to the inner surfaces of the liner using, for example, cold temperature adhesive. A base separator pad 6 is then mounted within the bottom of the outer box and adhered thereto using, for example, cold temperature adhesive. The inner insulating Expanded Polystyrene (EPS) foam container 7 is then inserted within the outer box and adhered thereto using, for example, cold temperature adhesive. Inner container 7 is then closed with lid 8, and outer container 4 is closed with lid 5. Finally, lid 1 fits over the liner 7 around the upper sections thereof in abutting relation to the upper edges of the outer box to complete the overall common container embodiment. The lid 1 is then sealed to the outer box 2 preferably with conventional packaging tape T as shown in FIG. 8.

The thermal enclosure of the common embodiment is most efficient as a cube system, but is not limited to cubes. The present invention may be embodied in other specific forms without departing from the main concept.

The preferred embodiment of the common embodiment includes the outer-shell container used for both species which starts with a rigid insulating box comprising a base portion and sides that extend from the base portion preferably connected from the same material sheet. Our most preferred embodiment would use B flute corrugated carton (tested at 200 lbs per square inch) however the same container can be manufactured from other corrugated, single or double-wall, pressed chipboard, wood based laminates, plastics, or metals without limitations of choice of materials. Further testing of such materials will demonstrate the best optional choices.

Figure 4:
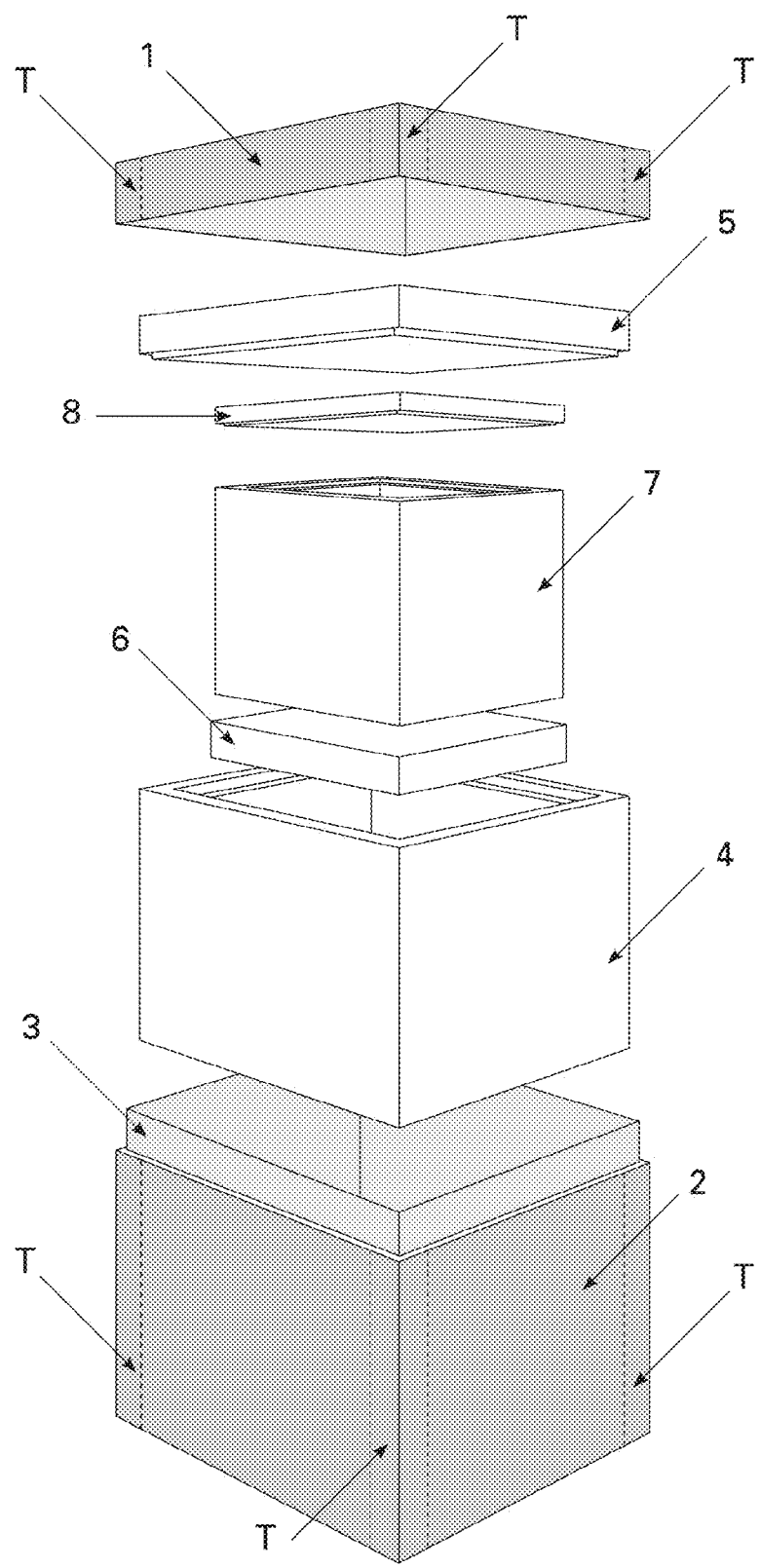

Referring to FIG. 5, a top view of the preferred single sheet design of the outer box is shown wherein the inside surfaces of the raised sides and the base portion join together to define the first enclosed space with the opening at an end that is opposite from the base. Referring to FIG. 4, these five panels are then connected preferably using reinforced tape T along all four vertical seam edges. The outer corrugated box is reinforced by the corrugated box liner 3 which then nests the large EPS container 4 that also nests the small EPS container 7. This four-layers nesting design ensures a minimum thickness of 3 inches of EPS insulating lateral walls and a minimum thickness of 5 inches bottom wall. The inner and outer EPS containers 4 and 7 also have the advantage of an additional EPS interim insulation liner pad 6 which helps maintain low temperatures by further separating the base of the assembly by limiting high-temperature contamination usually generated by ambient levels.

Referring to FIG. 7, a top view of the preferred single sheet design of the outer box lid is shown wherein the inside surfaces of the raised sides and the top portion join together to define an enclosed space with the opening at an end that is opposite from the top. Referring to FIG. 4, these five panels are then connected preferably using reinforced tape T along all four vertical seam edges. The matching lid 1 of the outer box, which is built similarly to the base box using a single sheet design as well, seals the outer box opening when placed on top edge-to-edge. The box and lid may also be manufactured using multiple pieces that can be attached using tape, fasteners, hinges, or glues without limitations of choice of assembly. However, test results have shown that such variations when compared to the single board concept are inferior mostly due to the seeping of cold air through the hairline cavities created by multi-piece assemblies. The complexity of single-piece manufacturing of the base box and its lid are greatly rewarded by the added performance of such critical temperature control conditions inside the containers.

FIG. 4 is an exploded view of the common container embodiment identifying the various component layers and clarifying the overall nesting assembly process. This view also shows the single sheet removable lid (1) that fits tight to seal the corrugated outer box (2) which is held and reinforced by the corrugated liner (3) that attaches inside the outer box along the four sides thereby reinforcing the corners and adding a second structure support layer. The preferred single sheet liner material in this case is the same B flute corrugated carton which once attached to the inside walls of the box exceeds the box rim to create a receiving edge for the single sheet lid. This view also shows the first and larger container (4) which provides a third insulating layer preferably made of high-density molded EPS which defines the main enclosed space or retention chamber comprising a separate tight-fitting removable lid (5) which completes the inside container. Other materials without limitations can be used to create this inside contents container however high insulation properties are necessary to achieve the required content shielding and tight seal capabilities.

The base separator pad (6) which provides a forth insulating layer preferably made of molded EPS as well and re-enhancing the thermal insulation properties of the overall assembly for cold temperature conditions and adding the equivalent of two additional base layers to the bottom of the contents containers when combined. The innermost contents container (7) providing a fifth insulating layer is the second and smaller container also preferably made of high-density molded EPS comprising another tight-fitting separate and removable lid (8) to complete this last part of the overall High-Performance Container System container assembly used with both disclosed inventions species. This second smaller EPS container is then nested inside the first larger EPS container thereby substantially preventing controlled cold air from communication with the outside. Other materials may be used to simulate the same level of insulation enhancement if chosen for any reason however none have been recently tested with equivalent R insulation values to the best of our knowledge. This efficient cube structure maximizes thermal performance of the insulating enclosure by minimizing thermal leakage from the corners and panel edges. Further insulation may also be provided by inserting thermal insulated panels between the outer shell and the larger EPS container.

This figure shows a summary of all nesting components that complete the preferred embodiment of the common container embodiment. Most preferred materials may be replaced with other materials and sizes and shapes of containers may be reconfigured to fit the users' requirements and their applications' needs almost without limitations and provided that the tight insulated enclosures of the main container is obtained and achieves the required internal temperature control conditions.

First Species: Target Refrigeration Temperature

The embodiment of the First Species adds to the Common Embodiment described above to provide and maintain a target refrigeration temperature range of 35° to 45° F. (2° to 8°

C.) to previously refrigerated payload. This target refrigeration temperature container additional setup illustrated in FIG. 8 which includes a passive coolant enclosure unit 9 consisting of a battery of multiple inner temperature controlling phase change material (hereafter "PCM") enclosures at a ratio further described in detail with respect to FIGS. 1a-d. Referring to FIG. 9, the setup allows sufficient spaces S to include desiccant pouches D on two sides of the coolant closure unit 9 for absorbing humidity generated during the temperature change cycle inside the container.

Another aspect of this embodiment includes a shielding protective panel 10 made of a honeycomb style perforated plastic that allows the free transfer of cold air from the cooling unit into the payload area to condition its content while protecting it from contact freezing. This protective panel also creates the enclosure necessary to keep the coolant unit from shifting inside the container when the container is moved.

Referring to FIGS. 12a-d, various views of the passive coolant enclosure unit 9 are illustrated. The unit 9 comprises a series of coolant containers a-e which are filled with freezable liquid gel. Although the drawings illustrate five containers, depending on the circumstances of the article to be transported, the number of containers could be varied.

Second Species: Target Freezing Temperature

The embodiment of the Second Species adds to the Common Embodiment described above to provide and maintain a target refrigeration temperature range of <32° F. (0° C.) to previously frozen payload. As illustrated in FIG. 13, the additional setup of this target refrigeration temperature container includes a passive coolant enclosure unit 11 consisting of one or a battery of multiple inner temperature controlling PCM enclosures filled with freezable liquid gel similar to the containers illustrated in FIG. 12. The freezing temperature requirements of this model also include a minimal amount of dry ice pellets 12 in a ratio that we further describe hereinafter. If a battery of multiple inner temperature controlling PCM enclosures are used, they would be placed in side-by-side relationship on the bottom, of inner container 7. If a one-piece battery having multiple inner temperature controlling PCM enclosures is used, it would have dimensions commensurate with the bottom of inner container 7.

Advantages of the Preferred Embodiments

The target achievement behind our disclosed species based on the following preferred embodiments is to secure a minimum 72 hours of refrigeration 35° to 45° F. (2° to 8° C.) or freezing<32° F. (0° C.) temperatures through two different models within average ambient conditions 68 to 84° F. (20 to 29° C.) and using a common custom insulating container design.

High-Performance Insulating Containers—Common Embodiment

The basis of our insulating container hereby known as the common embodiment is the design of a high-performance container capable of maintaining lightweight, rigidity, high capacity and small footprint, high insulation properties, recyclable, economical, and reusable.

With the evident notion that many uses and design variations are possible for, the following detailed descriptions explain the size variations options and materials alternatives. The described embodiments may be suitable for other applications given the benefits of the disclosures.

LIGHTWEIGHT—Although commonly used EPS shippers are typically light, our aim was to capitalize on known materials to maintain this feature. However, this weight limitation of common coolers sacrifices many other important features included in our goals of rigidity and reusability.

For these reasons, the preferred materials used to construct the common embodiment are limited to high-impact resistant corrugated cardboard and molded EPS foam. While this combination and its light weight matches materials that are typically used in the manufacturing of the "commonly used" EPS shippers, our container relies on the structure design to maximize on this combination of materials to provide the targeted rigidity feature.

RIGIDITY—Once again the combination of corrugated cardboard and EPS would usually limit the rigidity of the overall container and often jeopardize the integrity of the payload when their outer-shells are damaged as it frequently happens to "commonly used" EPS shippers. Other materials however may reduce this risk of breakage but can certainly add weight and often reduce the overall insulation properties of the assembly.

The structure design had to provide again the much needed rigidity of our common embodiment and ensure that payload volume and weight would not affect its performance.

CAPACITY & FOOTPRINT—High-performance insulation often means more materials if weight and cost are a concern. Typically, thicker walls may provide better R value however the best case structure also needs to maintain a small footprint while providing a generous space reserved for the payload area.

We reverse-engineered the process by evaluating an optimal capacity for the common embodiment then evaluated again the end results once cooling elements are added in each of the two models or species for various temperature control and maintenance. Keeping the footprint of the container is the new challenge at this point when weight is the second highest concern in the overall design. The structure design now also has to deliver the largest capacity with the smallest footprint.

INSULATION PROPERTIES—The focus on the use of corrugated cardboard and molded EPS foam may certainly address the weight feature and could provide rigidity if properly structured. This combination could also resolve the capacity and footprint concerns however high-performance insulation is the single utmost important property that the common embodiment must have in order to deliver the maximum performance time that we must achieve for both model requirements.

Thicker EPS container walls are insufficient and the corrugated shell hardly is an insulation factor. The structure design now has another essential property to deliver. Lightweight, rigid, high-capacity and small footprint features are basically useless without the high-performance insulation needed to ensure over 72 hours of maintained temperatures.

RECYCLABLE—The nature of the selected materials including corrugated cardboard and molded EPS foam have a limited life. However, both materials are made of recycled matters and may be recycled again after use. Other materials further used for the two species including refrigerant agents are mainly water-based environmentally friendly solutions that can be disposed of without any impact including recyclable plastic containers and separator shields.

Another challenging aspect of the structure design has to ensure that all accessory materials including adhesives when necessary and all other fasteners are environmentally friendly and/or recyclable materials as well.

ECONOMICAL—The cost factor drives the design of the common embodiment while features are conceived and developed then tested throughout the process. Both passive and "powered" coolant-based alternatives exist in various shapes and materials that can match and even exceed our targeted performance values. However, these options also come at a considerably higher price as we have identified solutions ranging from eight to twenty times the expected market price of our container including all necessary inner components that regulate the target temperatures of the two disclosed species.

The cost to the users must in this case be competitive to justify the return on investment by switching to this new technology and modify any logistics related details. Furthermore, our species must also provide a justifiable alternative through its performance to absorb the cost of discarded units for various reasons.

REUSABLE—Although most users of such technology typically recycle "commonly used" EPS shippers, another aspect of our species starting with the design of the common embodiment also focuses on rigidity and reusability when the end-use application allows. The structure of this common embodiment ensures multiple use cycles which is of utmost importance for storage applications and can also be considerably important for shipping as well. Point-to point users can easily return and reuse both species by replacing coolants in an organized way. However, this may remain an option for non-contaminating applications and totally up to the discretion of the end-users.

The cost to the technologies for both species can hereby be drastically reduced when the containers are reused and in good overall condition. The structure and all specific model elements are designed to help ensure that this feature is an integral part of both models through the common embodiment. Individual coolant elements may need to be replaced or reconditioned to maximize their performance.

STRUCTURE DESIGN—All above essential design features were kept in focus to create this common embodiment which achieved these proprietary specifications and resulted in the performance basis and the performance of the two species. The structure design customized all components as follows:

A. Corrugated cardboard outer-box lid—The outer-box lid is designed to minimize loss of cold air. Its single sheet pull-out design limits its closure seams to the four corners of the main box and abutting edges may be sealed using heavy-duty reinforced wide shipping tape. It is also designed to overlap by covering the inner liner thus greatly limiting air escape.

B. Corrugated cardboard outer-box—Like its lid, the corrugated cardboard outer-box is also formed of a single sheet. Its four corner seams once again play an important role to confine cold air inside the container and all four abutting edges may be sealed using heavy-duty reinforced wide shipping tape. Its double-wall assembly then improves its impenetrability while enhancing its rigidity.

C. Corrugated cardboard liner—This liner plays two roles as described above. It converts the outer-box into a double-wall corrugated container and multiplies its rigidity when glued to the outer sheet. It also extends beyond the top edge of the outer-box to create an overlap area that receives the corrugated lid to form a tighter enclosure to the whole assembly. This assembly is completed using cold temperature adhesives.

D. Large EPS insulating box—This first and larger of two EPS molded foam container provides the first thermal insulation barrier of the common embodiment structure. It is designed to be the thicker shield from the outside elements however it is more importantly the last protection layer of cold air. This first container is attached to the bottom of the outer corrugated box and to the inner cardboard liner walls also using cold temperature adhesives.

E. Large EPS insulating box lid—The large EPS container has a tight fitting lid designed to slide-in when inserted to close its cavity rather than fit over in order to limit the cold air escape as well. This combination of custom molded container and lid considerably insulates the payload and its refrigeration from the outside elements thus improving the performance of the coolants as well as the inner container.

F. EPS interim insulation liner pad—Cold air is proven to travel to the bottom and insulating it from the outside elements is a great concern as well in this case. The interim insulation pad is a thick molded EPS foam element that is designed to separate the bottoms of the two inner containers while multiplying their insulating capabilities by doubling the EPS foam layers. This pad slides in and attaches to the larger EPS container using cold temperature adhesives.

G. Small EPS inner box—This second and smaller of the two EPS molded foam container also referred to as the retention chamber provides the innermost thermal insulation of the common embodiment. It is designed to shield the payload from the outside elements but more importantly to maintain the cold temperatures of its preconditioned payload and refrigerants. Its base is attached to the top of the insulation pad and its outer walls to the inner walls of the larger EPS container thus transforming this assembly into a single container unit using cold temperature adhesives.

H. Small EPS inner box lid—The smaller EPS container has a tight fitting lid designed to slide-in when inserted to securely close its cavity rather than fit over thus limiting any cold air escape as well. This combination of custom molded container and lid adds considerable insulating capability to maintain the payload and its refrigeration from the outside elements thus improving the performance of the coolants.

First Species: Target Refrigeration Temperature

The present claimed invention is designed as a thermal storage and shipping container comprising the EPS inner enclosures which define the inner payload area and outer shells creating a robust and considerably airtight box. The model uses a cooling unit filled with PCM. The container has an outside shell made from corrugated cardboard or the like holding the interconnected cube shaped structure. Inserted snugly into the outer shell are two inner insulating containers. The insulation is preferably made of formed EPS also known as Styrofoam or the like, or any material having a high thermal resistance "R". Stored or shipped payload is typically placed in the innermost retention chamber and the thermal insulating enclosure is sealed and stored or shipped.

This embodiment of the First Species together with the Common Embodiment described above is designed to provide and maintains a target refrigeration temperature range of 35° to 45° F. (2° to 8° C.) to previously refrigerated payload. This target refrigeration temperature container assembly requires additional setup to the common embodiment as shown in FIGS. 8-10 which includes a passive coolant unit 9 consisting of a battery of multiple inner freeze gel or PCM enclosures.

Testing based on our preferred embodiment described herein proved the need for multiple 16 oz. freeze gel-packs PCM stacked to form a battery chain of frozen phase changing material. A ratio of 1:2.3 coolant mass to payload volume may be necessary to ensure the disclosed performance. Five 16 oz. freeze gel-packs inside the inner EPS container of our common embodiment consistently proved to maintain refrigeration temperature levels for over 72 hours when used to sustain up to 333 cubic inches of payload in the retention chamber under room temperature environment testing. These results triple the currently known performance of standard "shipping cooler" boxes used by our target market verticals.

This species and its coolant setup often require the addition of desiccant dehumidification in the form of packs or pouches to absorb the humidity generated during the temperature change cycle PCM inside the container. This protective step may be necessary especially when payload batch packaging is paper-based or made of penetrable materials.

Another aspect of this embodiment is the protective panel element 10 made of a honeycomb style perforated plastic mainly to allow the free transfer of cold air from the cooling unit into the payload area and condition its content and also to protect this payload from contact freezing. This shielding panel doubles to create the enclosure necessary to keep the coolant unit from shifting inside the container when the container is moved.

Preparing the first species embodiment for controlled temperature storage or shipping requires pre-freezing the PCM unit (hereby also referred to as battery). This coolant module is then placed at one end of the retention chamber then enclosed in its space using the shielding protective panel as shown in FIGS. 8-10. Desiccant pouches D are then added around the shorter ends of the cooling unit to absorb any humidity resulting from the PCM process. Payload is then introduced and stacked in the payload area as indicated and can be secured using foam peanuts or paper placed away from the shielded coolant side. The lid of the small EPS container is then secured in place followed by the lid of the larger EPS container and finally by the corrugated outer-box lid which slides in place to secure the assembly. The High-Performance Container System must be securely taped sealed once the full assembly is completed and all lids are in place including the outer lid. The abutting edges of the lid and box must be sealed using heavy-duty reinforced wide shipping tape in a ring fashion all around the box.

Second Species: Target Freezing Temperature

The second claimed invention is also designed as a thermal storage and shipping container comprising the EPS inner enclosures which define the inner payload area and outer shells creating a robust and considerably airtight box using the common embodiment described above. This model uses a cooling unit filled with PCM. The container has an outside shell made from corrugated cardboard or the like holding the interconnected cube shaped structure. Inserted snugly into the outer shell are two inner insulating containers. The insulation is preferably made of formed EPS also known as Styrofoam or the like, or any material having a high thermal resistance "R". Stored or shipped payload is typically placed in the innermost retention chamber and the thermal insulating enclosure is sealed and stored or shipped.

This embodiment of the Second Species together with the Common Embodiment described above is designed to provide and maintains a target freezing temperature range of <32° F. (<0° C.) to previously frozen payload. This target freezing temperature container assembly requires additional setup to the common embodiment as shown in FIGS. 13-16 which includes a passive relay coolant unit 11 consisting of one or multiple inner freeze gel or PCM enclosures. Furthermore, this embodiment requires the use of dry ice pellets to create and maintain the targeted sub-zero conditions inside the retention chamber. The relay coolant unit is also included in the freeze maintenance process as payload however kicks in when all the dry ice has evaporated to provide the extended coolant time factor.

Testing based on this preferred embodiment described herein proved the need for 48 oz. of freeze gel-packs PCM to cover the bottom of the innermost container or retention chamber with pre-conditioned (frozen) phase changing material base. A ratio of 1:2 coolant mass (PCM and dry ice) to payload volume may be necessary to ensure the disclosed performance. This coolant assembly along with 5 lbs of dry ice pellets inside the inner EPS container of our common embodiment consistently proved to maintain freezing temperature levels for over 72 hours when used to sustain up to 338 cubic inches of payload in the retention chamber under room temperature environment testing. These results triple the currently known performance of standard "shipping cooler" boxes used by our target market verticals.

This species and its coolant setup often require the addition of desiccant dehumidification in the form of packs or pouches to absorb the humidity generated during the temperature change cycle PCM inside the container. This protective step may be necessary especially when payload batch packaging is paper-based or made of penetrable materials.

Preparing the second species embodiment for controlled temperature storage or shipping requires pre-freezing the PCM unit (hereby also referred to as relay base). This coolant module is then placed inside the retention chamber and covers its bottom to form a full base as shown in FIGS. 13-16. Desiccant pouches are then added around the payload area to absorb any humidity resulting from the PCM process. Payload is then introduced and stacked over the dry ice and can be secured using foam peanuts or paper. It is also recommended to cover the payload with a sheet of paper to help extend the life of the dry ice. The lid of the smaller EPS container is then secured in place followed by the lid of the larger EPS container and finally by the corrugated outer-box lid which slides in place to secure the assembly. The High-Performance Container System must be securely taped sealed once the full assembly is completed and all lids are in place including the outer lid. The abutting edges of the lid and box must be sealed using heavy-duty reinforced wide shipping tape in a ring fashion all around the box.

The achieved testing results are based on the IATA regulation for acceptable and limited use of 5 lbs of dry ice per shipping container using airfreight transportation and based on the proper preparation of the payload specimens and other shipment preparation requirements and in mostly ambient temperature conditions. These results are already a high challenge when all known disposable EPS based shipping containers maintain dry ice for no more than 24 hours at best. Our invention capitalizes of the high freezing properties of commercially available dry ice and supports its life through our High-Performance Container System disclosed above with a PCM relay base. The use of additional dry ice in storage and ground transportation situations may extend the freezing temperature conditions to up to 90 hours when properly prepared.

The present inventions have been described with some degree of particularity directed to the exemplary embodiments thereof. They are defined by the claims using specific materials and accessories. All modifications or changes may be made to the preferred embodiments of the present inventions without departing from the inventive concepts contained herein however further performance testing would be necessary to ensure that such changes do not alter expected results that may nullify the concept.

What is claimed is:

1. A thermally insulated reusable and recyclable storage and transport system, comprising:

an outer substantially rigid container having a bottom wall and side walls extending upward from said bottom wall defining an open top, said bottom and side walls having interior and exterior surfaces;

a substantially rigid outer container lid having top and bottom surfaces sized and adapted to sealingly close said outer container open top;

a substantially rigid liner having interior and exterior surfaces, and mounted within said outer container, with said exterior surfaces of said liner being juxtaposed and directly abutting against said interior surfaces of said outer container side walls, said liner completely covering said interior surfaces of said outer container side walls;

said outer container walls, said outer container lid and said liner made of insulating material;

a first substantially rigid inner container mounted within said outer container and said first inner container having a bottom wall and side walls extending upward from said bottom wall of said first inner container defining an open top, said bottom and side walls of said first interior container having interior and exterior surfaces;

a substantially rigid first inner container lid having top and bottom surfaces sized and adapted to sealingly close said first inner container open top;

said exterior surface of said first inner container bottom wall being juxtaposed and directly abutting against said interior surface of said outer container bottom wall, and said outer surfaces of said first inner container side walls being juxtaposed directly abutting against said interior surfaces of said liner, an intermediate insulating pad having top and bottom surfaces mounted within said first inner container with said bottom surface of the intermediate insulating pad completely covering and being juxtaposed and directly abutting against said interior surface of said first interior container bottom wall;

a second substantially rigid inner box-like container mounted within said first inner container and having a bottom wall and side walls extending upward from said bottom wall of said second inner container defining an open top, said bottom and side walls of said second inner container having interior and exterior surfaces;

a substantially rigid second inner container lid having top and bottom surfaces sized and adapted to sealingly close said second inner container open top;

said exterior surface of said second inner container bottom wall being juxtaposed and directly abutting against said top surface of said intermediate pad and said outer surfaces of said second inner container side walls being juxtaposed and directly abutting against said interior surfaces of said first inner container side walls, said first inner container, said first lid, said second inner container, said second lid and said intermediate pad made of insulating material;

said outer container lid, when mounted on said outer container, having said outer container lid bottom surface being juxtaposed and directly abutting against said top surface of said first inner container lid, when said first inner container lid is mounted on said first inner container, and said bottom surface of said first inner container lid is juxtaposed and directly abutting against said top surface of said second inner container lid, when said second inner container lid is mounted on said second inner container;

said second inner container defining an article storage and transport compartment and a refrigeration compartment;

whereby said transport system comprises a thermally insulated closable container for storage and/or shipment of articles of at least medical and environmental specimens, chemicals, fluids, solid samples, tissue, and organs.

2. The transport system as claimed in claim 1, wherein said outer container walls, said outer container lid and said liner made of cardboard.

3. The transport system as claimed in claim 1, wherein said side and bottom walls of said first inner container wall, said first inner container lid, said side and bottom walls of said second inner container, said second inner container lid and said intermediate pad are comprised of expanded polystyrene.

4. The transport system as claimed in claim 1, wherein said liner having a height greater than the height of said outer container walls, and said outer container lid includes side walls extending downward and in overlapping relation to said liner and in abutting relation to said side walls of said outer container when said outer container lid is mounted on said outer container, said side walls of said outer container lid having interior and exterior surfaces with said interior surfaces being juxtaposed and directly abutting against said exterior surfaces of said liner and said exterior surfaces of said side walls of said outer container lid being collinear with said exterior surfaces of said outer container walls, whereby the abutment between said outer container lid side walls and said outer container side walls are adapted to be sealed by an adherent sealing strip or overlapping material for sealing said lid side walls to said outer container side walls.

5. The transport system as claimed in claim 4, wherein the height of said side walls of said first inner container are equal to the height of said liner.

6. The transport system as claimed in claim 1, wherein said materials are recyclable materials.

7. The transport system as claimed in claim 1, wherein the thickness between said exterior surface of said outer container side walls and said interior surface of said second inner container side walls is at minimum two inches, the thickness between said top surface of said outer container lid and said bottom surface of said second inner container lid is at minimum two inches, and the thickness between said second container bottom wall interior surface and said outer container bottom wall exterior surface of is at minimum three inches.

8. The transport system as claimed in claim 1, wherein said side walls of said first and second inner containers having upper edges defining ledges and said lids of said first and second inner containers having peripheral edges complementally configured to said upper edges such that each respective lid is nested within each respective container in a sealing manner.

9. The transport system as claimed in claim 1, wherein said outer container bottom and side walls are made from a single sheet with said side walls folded upward from said bottom wall thereby defining abutting side wall edges sealed to each other by an adhesive strip or flaps extending from respective side walls of said outer container overlapping an adjacent side wall and sealed thereto to enclose said side walls, and said outer container lid adapted to be sealed to each respective side wall of said outer container by an adhesive strip or overlapping material for sealing said lid to said side walls.

10. The transport system as claimed in claim 5, wherein said outer container lid is made from a single sheet with said side walls folded downward thereby defining abutting edges sealed to each other by an adhesive strip or flaps extending from respective side walls of said outer container lid overlapping an adjacent side wall and sealed thereto to enclose said side walls.

11. The transport system as claimed in claim 5, wherein said outer container bottom and side walls are made from a single sheet with said sidewalls folded upward from said bottom wall thereby defining abutting side wall edges sealed to each other by an adhesive strip or flaps extending from respective side walls of said outer container overlapping an adjacent side wall and sealed thereto to enclose said side walls.

12. The transport system as claimed in claim 11, wherein said outer container lid is made from a single sheet with said side walls folded downward thereby defining abutting edges sealed to each other by an adhesive strip or flaps extending from respective side walls of said outer container lid overlapping an adjacent side wall and sealed thereto to enclose said side walls.

13. The transport system as claimed in claim 1, wherein said adjacent surfaces of said outer container, said liner, said first inner container, said pad, and said second inner container are adhered to each other.

14. The transport system as claimed in claim 1, further comprising refrigerants within said refrigeration compartment for maintaining an internal temperature in said storage and transporting compartment between 35° to 45° F. (2° to 8° C.) for a period of at least 72 hours.

15. The transport system as claimed in claim 14, wherein said refrigerant comprise a passive coolant enclosure unit having a series of side-by-side, thermally communicating containers each containing temperature controlling phase change material therein.

16. The transport system as claimed in claim 15, wherein said controlling phase changing material is freezable liquid gel.

17. The transport system as claimed in claim 14, further comprising a perforated panel separating said refrigeration compartment from said storage compartment thereby protecting said article from said refrigerant and allowing free transfer of cool air from said refrigeration compartment into said storage compartment.

18. The transport system as claimed in claim 17, wherein said panel comprises a honeycomb style plastic sheet.

19. The transport system as claimed in claim 15, further comprising desiccant pouches disposed within said refrigeration compartment around said coolant enclosure unit for absorbing humidity generated during a temperature change cycle inside the transport system.

20. The transport system as claimed in claim 16, further comprising desiccant pouches disposed within said refrigeration compartment around said coolant enclosure unit for absorbing humidity generated during a temperature change cycle inside the transport system.

21. The transport system as claimed in claim 17, further comprising desiccant pouches disposed within said refrigeration compartment around said coolant enclosure unit for absorbing humidity generated during a temperature change cycle inside the transport system.

22. The transport system as claimed in claim 18, further comprising desiccant pouches disposed within said refrigeration compartment around said coolant enclosure unit for absorbing humidity generated during a temperature change cycle inside the transport system.

23. The transport system as claimed in claim (15, further comprising a perforated panel separating said refrigeration compartment from said storage and transport compartment thereby protecting said article from said refrigerant and allowing free transfer of cool air from said refrigeration compartment into said storage compartment.

24. The transport system as claimed in claim 23, wherein said panel comprises a honeycomb style plastic sheet.

25. The transport system as claimed in claim 24, further comprising desiccant pouches disposed within said refrigeration compartment around said coolant enclosure unit for absorbing humidity generated during a temperature change cycle inside the transport system.

26. The transport system as claimed in claim 1, further comprising refrigerants within said refrigeration compartment for maintaining an internal temperature in said storage and transporting compartment less than 32° F. (0° C.) for a period of at least 72 hours.

27. The transport system as claimed in claim 26, wherein said refrigerant comprise a single passive coolant enclosure unit having a series of side-by-side, spaced, thermally communicating compartments each containing temperature controlling phase change material therein, said single passive coolant enclosure unit disposed over said bottom wall of said second inner container, and said article storage compartment overlying said refrigeration compartment.

28. The transport system as claimed in claim 27, wherein said controlling phase changing material is freezable liquid gel.

29. The transport system as claimed in claim 27, further comprising said refrigeration compartment including a layer of dry ice disposed over said single enclosure unit.

30. The transport system as claimed in claim 29, further comprising desiccant pouches disposed within said article storage compartment for absorbing humidity generated during a temperature change cycle inside the transport system.

31. The transport system as claimed in claim 27, further comprising desiccant pouches disposed within said article storage compartment for absorbing humidity generated during a temperature change cycle inside the transport system.

32. The transport system as claimed in claim 28, further comprising said refrigeration compartment including a layer of dry ice disposed over said single enclosure unit.

33. The transport system as claimed in claim 32, further comprising desiccant pouches disposed within said article storage compartment for absorbing humidity generated during a temperature change cycle inside the transport system.

* * * * *